US007833744B2

(12) United States Patent
Flockhart et al.

(10) Patent No.: US 7,833,744 B2
(45) Date of Patent: Nov. 16, 2010

(54) METHODS TO EVALUATE CYTOCHROME P450 2C19 ISOENZYME ACTIVITY USING A BREATH TEST

(75) Inventors: David A. Flockhart, Indianapolis, IN (US); Zeruesenay Desta, Carmel, IN (US); Anil S. Modak, Haverhill, MA (US); Yasuhisa Kurogi, North Andover, MA (US)

(73) Assignee: Cambridge Isotope Laboratories, Inc., Andover, MA (US)

( * ) Notice: Subject to any disclaimer, the term of this patent is extended or adjusted under 35 U.S.C. 154(b) by 96 days.

(21) Appl. No.: 11/848,750

(22) Filed: Aug. 31, 2007

(65) Prior Publication Data

US 2008/0085240 A1    Apr. 10, 2008

Related U.S. Application Data

(60) Provisional application No. 60/841,999, filed on Sep. 1, 2006.

(51) Int. Cl.
*C12Q 1/26* (2006.01)
(52) U.S. Cl. .......................................... 435/25; 424/9.1
(58) Field of Classification Search .................. 435/25; 424/9.1
See application file for complete search history.

(56) References Cited

U.S. PATENT DOCUMENTS

2004/0229222 A1* 11/2004 Chui et al. ...................... 435/6
2007/0026480 A1*  2/2007 Modak et al. ................. 435/25

OTHER PUBLICATIONS

Bastien M. et al. Characterization of Cytochrome P450 2E1 Activity . . . Canadian J of Physiology and Pharmacology 76(7-8)756-763, 1998.*
Tateishi T. et al. Omeprazole Does Not Affect Measured CYP3A4 Acitvity Using the Erythromycin Breath Test. British J of Pharmacology 40:411-412, 1995.*
Klotz U. et al. CYP2C19 Polymorphism and Proton Pump Inhibitors. Basic & clinical Pharmacology & Toxicology. 95(1)2-8, 2004.*
Poolsup N. et al. Pharmacogenetics and Psychopharmacotherapy. J of Clinical Pharmacy and Therapeutics 25(3)197-220, 2000.*
Arefayene M. et al. Sequence Diversity and Functional Characterization of the 5'Regulatory Region of Human CYP2C19. Pharmacogenetics 13(4)199-206, 2003.*
Desta Z. et al. Rapid Identification of the Hepatic Cytochrome P450 2C19 Activity Using a Novel and Noninvasive Patoprazole Breath Test. J of Pharmacology and Experimental Therapeutics. 329(1)297-305, 2009.*
Tateishi, et al., "Omeprazole Does Not Affect Measured CYP3A4 Activity Using the Erythromycin Breath Test", *British J. Clinical Pharmacology*, Oct. 1995, vol. 40., pp. 411-412.
Furuta, et al; "CYP2C19 Genotype Status and Effect of Omeprazole on Intragastric pH in Humans", *Clin. Pharmacol. Ther.*, May 1999, vol. 65., pp. 552-561.

Desta, et al; "Clinical Significance of the Cytochrome P450 2C19 Genetic Polymorphism", *Clinical Pharmacokinetics*, 2002, vol. 41(12)., pp. 913-958.
International Search Report (PCT/US07/77362); Date of Mailing Mar. 20, 2008; 2 pages.
Goldstein, "Clinical Relevance of Genetic Polymorphisms in the Human CYP2C Subfamily", *Br. J. Clin. Pharmacol.*, Oct. 2001, vol. 52., pp. 349-355.
Demorais, et al., "Identification of a New Genetic Defect Responsible for the Polymorphism of (S)-Mephenytoin Metabolism in Japanese", *Mol. Pharmacol.*, Oct. 1994, vol. 46., pp. 594-598.
Ibeanu, et al., "Identification of New Human CYP2C19 Alleles (CYP2C19*6 and CYP2C19*2B) in a Caucasian Poor Metabolizer of Mephenytoin", *J. Pharmacol. Exp. Ther.*, Sep. 1998, vol. 286., pp. 1490-1495.
Ibeanu, et al., "An Additional Defective Allele, CYP2C19*5, Contributes to the S-Mephenytoin Poor Metabolizer Phenotype in Caucasians", *Pharmacogenetics*, Apr. 1998, vol. 8., pp. 129-135.
Ibeanu, et al., "A Novel Transversion in the Intron 5 Donor Splice Junction of CYP2C19 and a Sequence Polymorphism in Exon 3 Contribute to the Poor Metabolizer Phenotype for the Anticonvulsant Drug S-Mephenytoin", *J. Pharmacol. Exp. Ther.*, Aug. 1999, vol. 290., pp. 635-640.
Ferguson, et al., "A New Genetic Defect in Human CYP2C19: Mutation of the Initiation Codon Is Responsible for Poor Metabolism of S-Mephenytoin", *J. Pharmacol. Exp. Ther.*, Jan. 1998, vol. 284, pp. 356-361.
Sim, et al., "A Common Novel CYP2C19 Gene Variant Causes Ultrarapid Drug Metabolism Relevant for the Drug Response to Proton Pump Inhibitors and Antidepressants", *Clin, Pharmacol. Ther.*, Jan. 2006, vol. 79., pp. 103-113.
Lazarou, et al., "Incidence of Adverse Drug Reactions in Hospitalized Patients: A Meta-Analysis of Prospective Studies", *J. Amer. Med. Assoc.*, Apr. 1998, vol. 279., pp. 1200-1205.
Furuta, et al., "Effect of Genetic Differences in Omeprazole Metabolism on Cure Rates for Helicobacter Pylori Infection and Peptic Ulcer", *Ann. Intern. Med.*, Dec. 1998, vol. 129., pp. 1027-1030.
Furuta, et al., "Influence of CYP2C19 Pharmacogenetic Polymorphism on Proton Pump Inhibitor-Based Therapies", *Drug Metab. Pharmacokinet*, Jun. 2005, vol. 20., pp. 153-167.

(Continued)

*Primary Examiner*—Ralph Gitomer
(74) *Attorney, Agent, or Firm*—Foley & Lardner LLP; James F. Ewing; Michel Morency

(57) ABSTRACT

The present invention relates, generally to a method of determining and assessing cytochrome P450 2C19-related (CYP2Cl9) metabolic capacity in an individual mammalian subject via a breath assay, by determining the relative amount of $^{13}CO_2$ exhaled by the subject upon intravenous or oral administration of a $^{13}C$-labeled CYP2C19 substrate compound. The present invention is useful as a non-invasive, in vivo assay for evaluating CYP2C19 enzyme activity in a subject using the metabolite $^{13}CO_2$ in expired breath, to phenotype individual subjects and to determine the selection, optimal dosage and timing of drug administration.

22 Claims, 2 Drawing Sheets

OTHER PUBLICATIONS

Hulot, et al., "Cytochrome P450 2C19 Loss-of-Function Polymorphism is a Major Determinant of Clopidogrel Responsiveness in Healthy Subjects", *Blood*, Oct. 2006, vol. 108., pp. 2244-2247.

Roy, et al., "Development of a Substrate-Activity Based Approach to Identify the Major Human Liver P-450 Catalysts of Cyclophosphamide and Ifosfamide Activation Based on cDNA-Expressed Activities and Liver Microsomal P-450 Profiles", *Drug Metab. Dispos.*, Jun. 1997, vol. 27., pp. 655-666.

Rae, et al., "Triethylenethiophosphoramide is a Specific Inhibitor of Cytochrome P450 2B6: Implications for Cyclophosphamide Metabolism", *Drug. Metab. Dispos.*, May 2002, vol. 30., pp. 525-530.

Takada, et al., "Cytochrome P450 Pharmacogenetics as a Predictor of Toxicity and Clinical Responses to Pulse Cyclophosphamide in Lupus Nephritis", *Arthritis Rheum.*, Jul. 2004, vol. 50., pp. 2202-2210.

Lacroix, et al., "Glucose Naturally Labeled with Carbon-13: Use for Metabolic Studies in Man", *Science*, Aug. 1973, vol. 181., pp. 455-446.

Modak, "Breath Analysis for Clinical Diagnosis and Therapeutic Monitoring", A. Amann, D Smith (ed). World Scientific, Singapore, 2005, pp. 457-478.

\* cited by examiner

METHODS TO EVALUATE CYTOCHROME P450 2C19 ISOENZYME ACTIVITY USING A BREATH TEST

RELATED APPLICATIONS

This application claims the benefit of provisional application Ser. No. 60/841,999, filed Sep. 1, 2006, the contents of which are incorporated herewith by reference in their entireties.

BACKGROUND OF THE INVENTION

The CYP2C19 gene is mapped to chromosome 10 (10q24.1-q24.3) and contains nine exons that code for a microsomal protein consisting of 490 amino acids, CYP219 is expressed primarily in human liver, and to a smaller extent in several extra-hepatic tissues (e.g., gut-wall). Hepatic cytochrome P450 (CYP) 2C19 is an important enzyme in the metabolism of widely used drugs such as the proton pump inhibitors (omeprazole, esomeprazole, lansoprazole and pantoprazole), diazepam, phenyloin, proguanil, clopidogrel, voriconazole, nelfinavir and cyclophosphamide (Desta, Z. et al., *Clin. Pharmacokinet.*, 41:913-58, 2002). As a result of genetic polymorphisms in the CYP2C19 gene and nongenetic factors (e.g. drug interactions), wide interindividual variability is seen in the in vitro as well as in vivo activity of CYP2C19. This variability accounts for a significant part of the substantial differences in the clearance and response to the large number of drugs metabolized by this enzyme. Therefore, identification of the mechanisms and causes for interindividual variability in CYP2C19 activity and developing means to prospectively predict them is important to optimize therapy with its substrates.

Conventional medical approaches to diagnosis and treatment of disease is based on clinical data alone, or made in conjunction with a diagnostic test. These traditional practices often lead to therapeutic choices that are not optimal for the efficacy of the prescribed drug therapy or to minimize the likelihood of side effects for an individual subject. Therapy-specific diagnostics (a.k.a., theranostics) is an emerging medical technology field that provides tests useful to diagnose a disease, choose the correct treatment regime, and monitor a subject's response. That is, theranostics are useful to predict and assess drug response in individual subjects, i.e., individualized medicine. Theranostic tests are useful to select subjects for treatments that are particularly likely to benefit from the treatment or to provide an early and objective indication of treatment efficacy in individual subjects, so that the treatment can be altered with a minimum of delay. Theranostic tests may be developed in any suitable diagnostic testing format, which include, but is not limited to, e.g., non-invasive breath tests, immunohistochemical tests, clinical chemistry, immunoassay, cell-based technologies, and nucleic acid tests.

There is a need in the art for a reliable theranostic test to define a subject's phenotype or the drug metabolizing capacity to enable physicians to individualize therapy thereby avoiding potential drug related toxicity in poor metabolizers and increasing efficacy. Accordingly, there is a need in the art to develop new diagnostic assays useful to assess the metabolic activity of drug metabolizing enzymes such as the cytochrome P450 enzymes (CYPs) in order to determine individual optimized drug selection and dosages.

SUMMARY OF THE INVENTION

The present invention relates to a diagnostic, noninvasive, in vivo phenotype test to evaluate CYP2C19 activity using a CYP2C19 substrate compound labeled with a detectable isotope incorporated at least at one specific position. The present invention utilizes the CYP2C19 enzyme-substrate interaction such that there is release of, for example, stable isotope-labeled $CO_2$ (e.g., $^{13}CO_2$) in the expired breath of a mammalian subject. The subsequent quantification of stable isotope-labeled $CO_2$ allows for the indirect determination of pharmacokinetics of the substrate and the evaluation of CYP2C19 enzyme activity (i.e., CYP2C19-related metabolic capacity).

In one aspect, the invention is directed to a preparation for determining CYP2C19-related metabolic capacity, comprising as an active ingredient a CYP2C19 substrate compound in which at least one of the carbon or oxygen atoms is labeled with an isotope, wherein the preparation is capable of producing isotope-labeled $CO_2$ after administration to a mammalian subject. In one embodiment of the preparation, the isotope is at least one isotope selected from the group consisting of: $^{13}C$; $^{14}C$; and $^{18}O$.

In another aspect, the invention is directed to a method for determining cytochrome P450 2C19 isoenzyme-related metabolic capacity, comprising administering to a mammalian subject a preparation comprising as an active ingredient a cytochrome P450 2C19 isoenzyme substrate compound in which at least one of the carbon or oxygen atoms is labeled with an isotope, wherein the preparation is capable of producing isotope-labeled $CO_2$ after administration to a mammalian subject, and measuring the excretion pattern of an isotope-labeled metabolite excreted from the body of the subject. In a particular embodiment, the isotope-labeled metabolite is excreted from the body as isotope-labeled $CO_2$ in the expired air.

In another embodiment, the invention is directed to a method for determining cytochrome P450 2C19 isoenzyme-related metabolic capacity in a mammalian subject, comprising administering to the mammalian subject a preparation comprising as an active ingredient a cytochrome P450 2C19 isoenzyme substrate compound in which at least one of the carbon or oxygen atoms is labeled with an isotope, wherein the preparation is capable of producing isotope-labeled $CO_2$ after administration to a mammalian subject, measuring the excretion pattern of an isotope-labeled metabolite excreted from the body of the subject, and assessing the obtained excretion pattern in the subject. In a particular embodiment, the method further comprises comparing the obtained excretion pattern in the subject or a pharmacokinetic parameter obtained therefrom with the corresponding excretion pattern or parameter in a healthy subject with a normal cytochrome P450 2C19 isoenzyme-related metabolic capacity.

In another embodiment, the invention is directed to a method for determining the existence, nonexistence or degree of cytochrome P450 2C19 isoenzyme-related metabolic disorder in a mammalian subject, comprising administering to the mammalian subject a preparation comprising as an active ingredient a cytochrome P450 2C19 isoenzyme substrate compound in which at least one of the carbon or oxygen atoms is labeled with an isotope, wherein the preparation is capable of producing isotope-labeled $CO_2$ after administration to a mammalian subject, measuring the excretion pattern of an isotope-labeled metabolite excreted from the body of the subject, and assessing the obtained excretion pattern in the subject.

In yet another embodiment, the invention is directed to a method for selecting a prophylactic or therapeutic treatment for a subject, comprising: (a) determining the phenotype of the subject; (b) assigning the subject to a subject class based on the phenotype of the subject; and (c) selecting a prophylactic or therapeutic treatment based on the subject class, wherein the subject class comprises two or more individuals who display a level of cytochrome P450 2C19 isoenzyme-related metabolic capacity that is at least about 10% lower than a reference standard level of cytochrome P450 2C19 isoenzyme-related metabolic capacity. In a particular embodiment, the subject class comprises two or more individuals who display a level of cytochrome P450 2C19 isoenzyme-related metabolic capacity that is at least about 10% higher than a reference standard level of cytochrome P450 2C19 isoenzyme-related metabolic capacity. In another embodiment, the subject class comprises two or more individuals who display a level of cytochrome P450 2C19 isoenzyme-related metabolic capacity within at least about 10% of a reference standard level of cytochrome P450 2C19 isoenzyme-related metabolic capacity. In one embodiment, the treatment is selected from the group consisting of: administering a drug, selecting a drug dosage and selecting the timing of a drug administration.

In another embodiment, the invention is directed to a method for evaluating cytochrome P450 2C19 isoenzyme-related metabolic capacity, comprising administering a $^{13}$C-labeled cytochrome P450 2C19 isoenzyme substrate compound to a mammalian subject, measuring $^{13}CO_2$ exhaled by the subject, and determining cytochrome P450 2C19 isoenzyme-related metabolic capacity from the measured $^{13}CO_2$. In one embodiment, the $^{13}$C-labeled cytochrome P450 2C19 isoenzyme substrate compound is a $^{13}$C-labeled pantoprazole or $^{13}$C-labeled omeprazole. In one embodiment, the $^{13}$C-labeled cytochrome P450 2C19 isoenzyme substrate compound is administered non-invasively, intravenously or orally. In one embodiment, the exhaled $^{13}CO_2$ is measured spectroscopically, e.g., by infrared spectroscopy, or with a mass analyzer. In a particular embodiment, the exhaled $^{13}CO_2$ is measured over at least three time periods to generate a dose response curve, and the cytochrome 2C19 isoenzyme-related metabolic activity is determined from the area under the curve. In another embodiment, the exhaled $^{13}CO_2$ is measured over at least three time periods to calculate a delta over baseline (DOB), and the cytochrome 2C19 isoenzyme-related metabolic activity is determined from the DOB. In another embodiment, the exhaled $^{13}CO_2$ is measured over at least three time periods to calculate a percentage dose recovery (PDR), and the cytochrome 2C19 isoenzyme-related metabolic activity is determined from the PDR. In one embodiment, the exhaled $^{13}CO_2$ is measured over at least two different dosages of the $^{13}$C-labeled cytochrome P450 2C19 isoenzyme substrate compound. In another embodiment, the exhaled $^{13}CO_2$ is measured during at least the following time points: $t_0$, a time prior to ingesting the $^{13}$C-labeled cytochrome P450 2C19 isoenzyme substrate compound; $t_1$, a time after the $^{13}$C-labeled cytochrome P450 2C19 isoenzyme substrate compound has been absorbed in the bloodstream of the subject; and $t_2$, a time during the first elimination phase. In one embodiment, the cytochrome P450 2C9 isoenzyme-related metabolic capacity is determined from as the a slope of $\delta^{13}CO_2$ at time points $t_1$ and $t_2$ calculated according to the following equation: slope=$[(\delta^{13}CO_2)_2-(\delta^{13}CO_2)_1]/(t_2-t_1)$ wherein $\delta^{13}O_2$ is the amount of exhaled $^{13}CO_2$. In a particular embodiment, at least one cytochrome P450 2C19 isoenzyme modulating agent, e.g., a cytochrome P450 2C19 inhibitor or a cytochrome P450 2C19 inducer, is administered to the subject before administrating a $^{13}$C-labeled cytochrome P450 2D6 isoenzyme substrate compound.

In another embodiment, the invention is directed to a method of selecting a mammalian subject for inclusion in a clinical trial for determining the efficacy of a compound to prevent or treat a medical condition, comprising: (a) administering a $^{13}$C-labeled cytochrome P450 2C19 isoenzyme substrate compound to the subject; (b) measuring a metabolite excretion pattern of an isotope-labeled metabolite excreted from the body of the subject; (c) comparing the obtained metabolite excretion pattern in the subject to a reference standard excretion pattern; (d) classifying the subject according to a metabolic phenotype selected from the group consisting of: poor metabolizer, intermediate metabolizer, extensive metabolizer, and ultrarapid metabolizer, based on the obtained metabolite excretion pattern; and (e) selecting the subject classified as extensive metabolizer in step (d) for inclusion in the clinical trial. In a particular embodiment, the isotope-labeled metabolite excreted from the body of the subject is isotope-labeled $CO_2$ in the expired air.

In another embodiment, the invention is directed to a kit comprising a $^{13}$C-labeled cytochrome P450 2C19 isoenzyme substrate compound and instructions provided with the substrate that describe how to determine $^{13}$C-labeled cytochrome P450 2C19 isoenzyme substrate compound metabolism in a subject. In a particular embodiment, the kit further comprises at least three breath collection bags. In another embodiment, the kit further comprises a cytochrome P450 2C19 modulating agent.

DETAILED DESCRIPTION OF THE INVENTION

Figure 1:
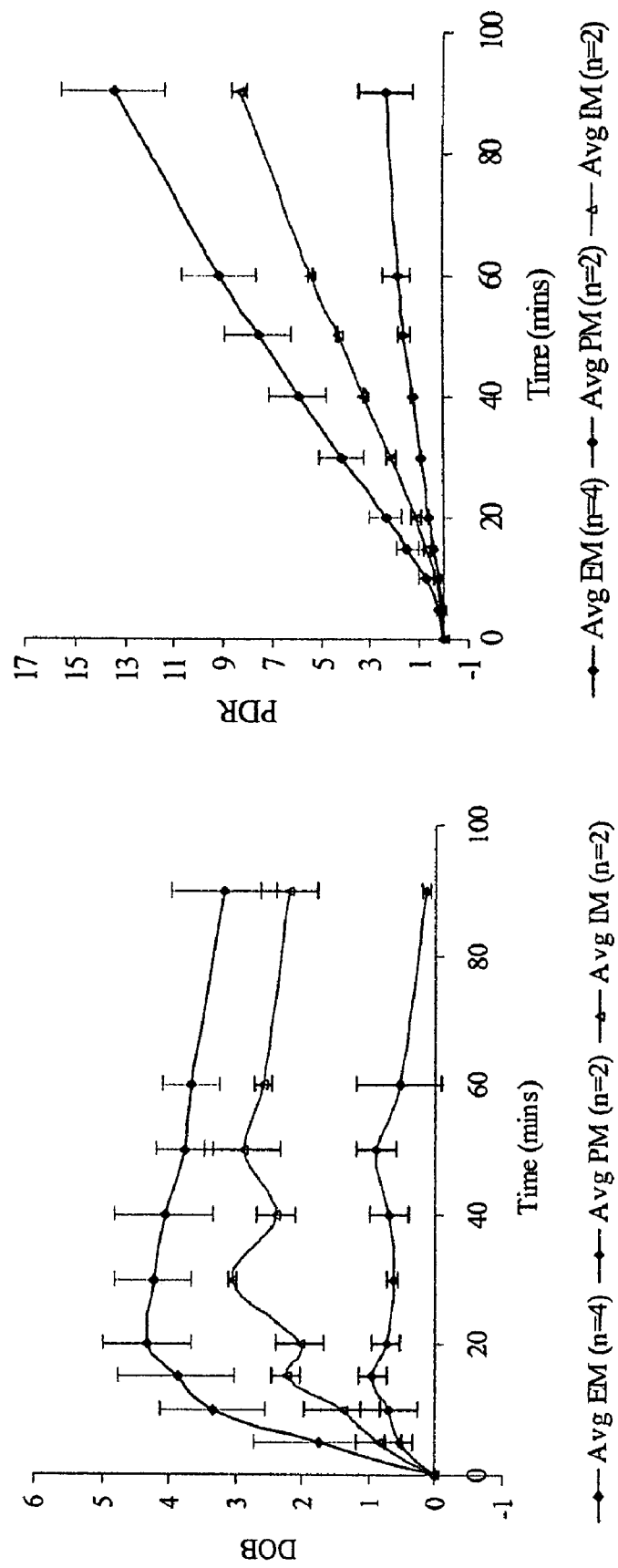
FIG. 1 shows breath curves (delta over baseline (DOB) versus time (left panel) and percentage dose recovery (PDR) curves versus time (right panel) for eight volunteers for the Ptz O$^{13}$CH$_3$ breath test.

The discovery of the first poor metabolizer (PM) of mephenytoin in 1979 and the subsequent demonstration of the genetic basis for this phenotype have spurred extensive research into the genetic basis for the interindividual variations of (S)-mephenytoin 4-hydroxylation (CYP2C 19) and the role that this enzyme plays in human drug metabolism. On the basis of the ability to metabolize (S)-mephenytoin (or other CYP2C19 substrates), individuals can be classified as extensive metabolizers (EMs) or poor metabolisers (PMs) of CYP2C19. It is now established that the high interindividual and interethnic variability in the pharmacokinetics of CYP2C19 substrates is mainly due to polymorphisms in the CYP2C19 gene (Goldstein, J., Br. J. Clin. Pharmacol., 52:349-55, 2001). Over 25 alleles and allelic variants of CYP2C19 have been described. Most of these variants are null alleles (e.g., CYP2C19*2, *3, *4, *5, *6, *7 and *8) that result in complete absence of enzyme function (De Morais, S. et al., Mol. Pharmacol., 46:594-8, 1994; De Morais, S. et al., J. Biol. Chem., 1994; 269:15419-22; Ibeanu, G. et al., J. Pharmacol. Exp. Ther., 286:1490-5, 1998; Ibeanu, G. et al., Pharmacogenetics, 8:129-35, 1998; Ibeanu, G. et al., J. Pharmacol. Exp. Ther., 290:635-40, 1999; Ferguson, R. et al., J. Pharmacol. Exp. Ther., 284:356-61, 1998) while others result in either reduced (e.g.,*9, *11, *13) or increased activity (CYP2C19*17) (Sim, S. et al., Clin. Pharmacol. Ther., 79:103-13, 2006). Of these variants, the most frequent and functionally relevant alleles are CYP2C19*2 (CYP2C19m1) and CYP2C19*3 (CYP2C19m2). In both variants, a premature stop codon resulting in truncated and inactive enzyme or a truncated protein that is unable to bind to the haem moiety is produced. CYP2C19*2 is a single base pair G681A mutation in exon 5 of CYP2C19. CYP2C19*3 is a single base pair G636A mutation in exon 4 of CYP2C19 that results in a premature stop codon. Several studies indicate that the distribution of these common alleles is different among different populations. For example, the frequency of CYP2C19*2 has been reported to be ~17%, 30% and ~15% in African-Americans, Chinese and Caucasians, respectively, and the CYP2C19*3 allele was shown to be more frequent in Asians (~5%) than in Caucasians (0.04%) and Blacks (0.4%). These two alleles account for almost all PMs in Asian and Black African populations. CYP2C19*2 accounts for approximately 75 to 85% of variant alleles responsible for PMs in Asians and Caucasians. While CYP2C19*3 is extremely rare in Caucasian populations, it accounts for almost all the remaining defective alleles in Asians. Accordingly, there is a considerable interethnic heterogeneity in the frequency of PMs. Population distribution of CYP2C19 poor metabolizers (determined by phenotype and genotype) show that the Asian population had a higher incidence of CYP2C19 poor metabolizers (up to 25% in some studies), while in other populations except Vanuatu islands in eastern Melanesia (38-70%) it is below 8% (Desta, Z. et al., Clin. Pharmacokinet., 41:913-58, 2002).

In addition to genetic polymorphisms, other factors contribute to the interindividual variability in activity of CYP2C19. These factors include exposure to inhibitor or inducer drugs or other chemicals influence CYP2C19 activity. For example, drugs such as omeprazole, meclobemide, ticlopidine, clopidogrel, fluvoxamine and oral contraceptives are known to significantly impair CYP2C19 activity, while rifampin, efavirenz, ritonavir and St. John's wort enhance the clearance of its substrates. In addition, age, pregnancy, cancer, liver and inflammatory diseases appear to reduce the activity of CYP2C19 activity in vivo in humans.

Many therapeutic compounds are effective in about 30-60% of patients with the same disease. Further, a subset of these patients may suffer severe side effects, which are among the leading cause of death in the United States and have an estimated $100 billion annual economic impact (Lazarou, J. et al., Amer. Med. Assoc., 279:1200-1205, 1998). Many studies have shown that patients differ in their pharmacological and toxicological reactions to drugs due, at least in part, to genetic polymorphisms that contribute to the relatively high degree of uncertainty inherent in the treatment of individuals with a drug. Single nucleotide polymorphisms (SNPs)—variations in DNA at a single base that are found in at least 1% of the population—are the most frequent polymorphisms in the human genome. Such subtle changes in the primary nucleotide sequence of a gene encoding a pharmaceutically-important protein may be manifested as significant variation in expression, structure and/or function of the protein.

CYP 2C19 is involved in the biotransformation of close to 30 therapeutic drugs including proton pump inhibitors as summarized in Table 1. Isotopic labeling of the CYP2C19 substrates of Table 1 such that administration of the isotope-labeled substrate to a subject results in the release of stable isotopically-labeled $^{13}CO_2$ yields compounds useful in the methods of the present invention.

TABLE 1

| 2C19 substrates | 2C19 inhibitors | 2C19 inducers |
| --- | --- | --- |
| amitriptyline | cimetidine | carbamazepine |
| chloramphenicol | felbamate | norethindrone |
| citalopram | fluoxetine | prednisone |

TABLE 1-continued

| 2C19 substrates | 2C19 inhibitors | 2C19 inducers |
| --- | --- | --- |
| clomipramine | fluvoxamine | rifampin |
| cyclophosphamide | indomethacin | |
| diazepam | ketoconazole | |
| E-3810 | lansoprazole | |
| escitalopram | modafinil | |
| hexobarbital | omeprazole | |
| imipramine | probenicid | |
| indomethacin | ticlopidine | |
| lansoprazole | topiramate | |
| S-mephenytoin | | |
| R-mephobarbital | | |
| moclobemide | | |
| nelfinavir | | |
| nilutamide | | |
| omeprazole | | |
| oxcarbazepine | | |
| pantoprazole | | |
| phenytoin | | |
| phenobarbitone | | |
| primidone | | |
| progesterone | | |
| proguanil | | |
| propranolol | | |
| rabeprazole | | |
| r-warfarin | | |
| teniposide | | |

Select agents can induce or inhibit CYP2C19 activity (i.e., CYP 2C19 modulating agents). CYP modulating agents are important in the present invention as they can induce (increase) or inhibit (decrease) CYP 2C19 enzyme activity. Compounds known to inhibit and induce CYP 2C19 are summarized in Table 1.

It is to be appreciated that certain aspects, modes, embodiments, variations and features of the invention are described below in various levels of detail to provide a substantial understanding of the present invention. The present invention relates to a diagnostic, noninvasive, in vivo phenotype test to evaluate CYP2C19 activity, using a CYP2C19 substrate compound labeled with isotope incorporated at least at one specific position. The present invention utilizes the CYP2C19 enzyme-substrate interaction such that there is release of stable isotope-labeled $CO_2$ (e.g., $^{13}CO_2$) in the expired breath of a mammalian subject. The subsequent quantification of stable isotope-labeled $CO_2$ allows for the indirect determination of pharmacokinetics of the substrate and the evaluation of CYP2C19 enzyme activity (i.e., CYP2C19-related metabolic capacity based on the oral or i.v. administration of a stable isotope $^{13}C$-labeled CYP2C19 substrate compound and measurement of the $^{13}CO_2/^{12}CO_2$ ratio in expired breath using commercially available instrumentation, e.g., mass or infrared (IR) spectrometers.

The clinical relevance of CYP2C19 genetic polymorphisms has been recently demonstrated. It is well established that in EMs approximately 80% of doses of the proton pump inhibitors (PPIs) such as omeprazole, lansoprazole and pantoprazole are cleared by CYP2C19; about six-fold higher exposure to these drugs is observed in PMs than in EMs of (CYP2C19 and as a result PMs achieve greater acid suppression (Furuta, T. et al., Clin. Pharmacol. Ther., 65:552-561, 1999). The first report that CYP2C19 genotyping might influence clinical response to PPIs came from Furuta et al., who showed that treatment with omeprazole 20 mg/day plus amoxicillin brought about eradication of H. pylori infection in 28.6, 60 and 100% of homozygous EMs, heterozygous EMs and PMs of CYP2C19, respectively, and that this cure rate was parallel with the healing rates for both duodenal and gastric ulcers in the respective three groups (Furuta, T. et al., *Ann. Intern. Med.,* 129:1027-30, 1998). Several subsequent studies have established that patients who carry CYP2C19 genetic variants respond better than those who carry the wild-type allele (Furuta, T. et al., *Drug Metab. Pharmacokinet.,* 20:153-67, 2005). Therefore, genotyping for the common alleles of CYP2C19 before initiating PPIs for the treatment of reflux disease and *H. pylori* infection has been suggested to be a cost effective tool to select appropriate duration of treatment and dosage regimens.

Other drugs that are significantly influenced by CYP2C19 genotype include the anti-platelet drug clopidogrel and the anticancer drug cyclophosphamide. Clopidogrel is a widely used drug in the prevention and treatment of thrombotic complications following stroke, unstable angina, myocardial infarction and coronary stent placement. Clopidogrel is a prodrug that requires conversion to active metabolite by the CYP system before it exerts its anti-platelet effects. The lack or diminished anti-platelet response in a substantial number of patients receiving clopidogrel is a major problem during its clinical use.

A recent report indicate that clopidogrel had no anti-platelet effect in healthy volunteers who carry CYP2C19*2 compared to those who carry CYP2C19*1*1 genotype (Hulot, J. et al., *Blood,* 108:2244-7, 2006). This observation implies clopidogrel nonresponsive platelets are at risk for thrombotic events, with devastating outcome to the patient. Similarly, cyclophosphamide is a prodrug that requires metabolic activation by cytochrome P450 (CYP) enzymes to 4-hydroxycyclophosphamide. Multiple CYPs have been implicated in this activation (Roy, P. et al., *Drug Metab. Dispos.,* 27:655-66, 1997; Rae, J. et al., *Drug Metab. Dispos.,* 30:525-30, 2002), including CYP2A6, 2B6, 2C19, 2C9, 3A4, and 3A5, but CYP2C19 appears to be a key enzyme particularly at low cyclophosphamide concentrations. For lupus nephritis patients taking cyclophosphamide, it was found that CYP2C19*2 is a predictor of premature ovarian failure and progression to end-stage renal failure (Takada, K. et al, *Arthritis Rheum.,* 50:2202-10, 2004).

Given the clinical relevance of this enzyme, it would be important to develop a diagnostic test that identifies and predicts a subgroup of patients who are at high-risk for failure of therapy during initiation of CYP2C19 substrates such as clopidogrel, cyclophosphamide and proton-pump inhibitors. Reliable genotype tests are now commercially available to assay CYP2C19 variants (e.g., Roche AmpliChip), but they do not capture differences in CYP2C19 activity fully, as non-genetic factors have important effects on CYP2C19 activity in vivo in humans. In vivo phenotypic tests that can capture both genetic and non-genetics causes of variable CYP2C19 function have been instrumental to better understand the role of genetic and nongenetic factors on CYP2C19 function (e.g., S-mephenytoin 4-hydroxylation or omeprazole 5-hydroxylation) (Desta, Z. et al., *Clin. Pharmacokinet.,* 41:913-58, 2002). Their use for dose adjustment or selection of appropriate drugs, however, is very limited in part because they are often expensive, time and resource intensive and invasive (requires pharmacokinetic sampling). Therefore, a quick, simple and noninvasive method that can assess CYP2C19 phenotype is needed prior to prescribing of CYP2C19 substrate drugs.

The mammalian liver plays a primary role in the metabolism of steroids, the detoxification of drugs and xenobiotics, and the activation of procarcinogens. The liver contains enzyme systems, e.g., the CYP system, which converts a variety of chemicals to more soluble products. The CYPs are among the major constituent proteins of the liver mixed function monooxygenases. There are a number of classes of CYPs that include the hepatic isoenzymes, e.g., CYP3As (40-60% hepatic P-450 isoenzymes); CYP2D6 (2-5% hepatic P-450 isoenzymes), CYP1A2, CYP2Cs. The action of CYPs facilitates the elimination of drugs and toxins from the body. Indeed, CYP action is often the rate-limiting step in pharmaceutical elimination. CYPs also play a role in the conversion of prodrugs to their biologically active metabolites.

The CYPs are quantitatively the most important phase I drug biotransformation enzymes and genetic variation of several members of this gene superfamily has been examined. In phase I metabolism of drugs and environmental pollutants, CYPs often modify substrate with one or more water-soluble groups (such as hydroxyl), thereby rendering it vulnerable to attack by the phase II conjugating enzymes. The increased water-solubility of phase I and especially phase II products permits ready excretion. Consequently, factors that lessen the activity of CYPs usually prolong the effects of pharmaceuticals, whereas factors that increase CYP activity have the opposite effect.

Since the use of the naturally occurring $^{13}C$ compound $^{13}C$-glucose for a metabolic study in humans was described in 1973 (Lacroix, M. et al., *Science,* 181:445-6, 1973), stable isotope $^{13}C$-labeled compounds have been widely used as diagnostic probes in research laboratories for over 30 years (Modak, *Breath Analysis For Clinical Diagnosis and Therapeutic Monitoring.* A. Amann, D Smith (ed). pp 457-478. World Scientific, Singapore (2005). 2005). Subsequent to the wide availability of low cost $^{13}C$-substrates and the development of non-dispersive isotope selective IR spectrometry (NDIRS) as opposed to previous quantitation methods (e.g., mass spectrometry detection or other complicated analytical assays), diagnostic $^{13}C$ stable isotope probes are increasingly used to provide precise evaluations of the presence or absence of etiologically, significant changes in metabolism due to a specific disease or the lack of a specific enzyme but also in assessing the metabolic status of drug metabolizing enzymes.

Select Clinical Applications of the Method of the Invention

1. Correlating a Subject to a Standard Reference Population

One aspect of the invention relates to diagnostic assays for determining CYP2C19-related metabolic capacity, in the context of a biological sample (e.g., expired air) to thereby determine whether an individual is afflicted with a disease or disorder, or is at risk of developing a disorder, associated with aberrant CYP2C19 expression or activity. To deduce a correlation between clinical response to a treatment and a gene expression pattern or phenotype, it is necessary to obtain data on the clinical responses exhibited by a population of individuals who received the treatment, i.e., a clinical population. This clinical data can be obtained by retrospective analysis of the results of a clinical trial. Alternatively, the clinical data can be obtained by designing and carrying out one or more new clinical trials. The analysis of clinical population data is useful to define a standard reference population, which, in turn, are useful to classify subjects for clinical trial enrollment or for selection of therapeutic treatment. It is preferred that the subjects included in the clinical population have been graded for the existence of the medical condition of interest, e.g., CYP2C19 PM phenotype, CYP2C19 IM phenotype, CYP2C19 EM phenotype, or CYP2C19 UM phenotype. Grading of potential subjects can include, e.g., a standard physical exam or one or more tests such as the breath test of the present invention. Alternatively, grading of subjects can include use of a gene expression pattern, e.g., CYP2C19 allelic variants. For example, gene expression pattern is useful as grading criteria where there is a strong correlation between gene expression pattern and phenotype or disease susceptibility or severity.

ANOVA is used to test hypotheses about whether a response variable is caused by, or correlates with, one or more traits or variables that can be measured. Such standard reference population comprising subjects sharing gene expression pattern profile and/or phenotype characteristics, are useful in the methods of the present invention to compare with the measured level of CYP2C19-related metabolic capacity or CYP2C19 metabolite excretion pattern in a given subject. In one embodiment, a subject is classified or assigned to a particular genotype group or phenotype class based on similarity between the measured expression pattern of CYP2C19 metabolite and the expression pattern of CYP2C19 metabolite observed in a reference standard population. The method of the present invention is useful as a diagnostic method to identify an association between a clinical response and a genotype or haplotype (or haplotype pair) for the CYP2C19 gene or a CYP2C19 phenotype. Further, the method of the present invention is useful to determine those individuals who will or will not respond to a treatment, or alternatively, who will respond at a lower level and thus may require more treatment, i.e., a greater dose of a drug.

2. Monitoring Clinical Efficacy

The method of the present invention is useful to monitoring the influence of agents (e.g., drugs, compounds) on the expression or activity of CYP2C19-related metabolic capability and can be applied in basic drug screening and in clinical trials. For example, the effectiveness of an agent determined by a CYP2C19 phenotype assay of the invention to increase CYP2C19-related metabolic activity can be monitored in clinical trials of subjects exhibiting decreased CYP2C19-related metabolic capability. Alternatively, the effectiveness of an agent determined by a CYP2C19 phenotype assay of the invention to CYP2C19-related metabolic activity can be monitored in clinical trials of subjects exhibiting increased CYP2C19-related metabolic capacity.

Alternatively, the effect of an agent on CYP2C19-related metabolic capability during a clinical trial can be measured using the CYP2C19 phenotype assay of the present invention. In this way, the CYP2C19 metabolite expression pattern measured using the method of the present invention can serve as a benchmark, indicative of the physiological response of the subject to the agent. Accordingly, this response state of a subject can be determined before, and at various points during treatment of the individual with the agent.

The following Examples are presented in order to more fully illustrate the preferred embodiments of the invention. These Examples should in no way be construed as limiting the scope of the invention, as defined by the appended claims.

EXAMPLES

Example 1

Classification of Human Subject by Pantoprazole (Ptz) Metabolic Capacity Using the $^{13}CO_2$ Breath Test Method of the Invention The semisynthetic proton pump inhibitor pantoprazole (Ptz) is useful to suppress acid production in the stomach. Ptz metabolism is genetically polymorphous, CYP2C19 mediates the O-demethylation of Ptz-O-$^{13}CH_3$ as detailed below.

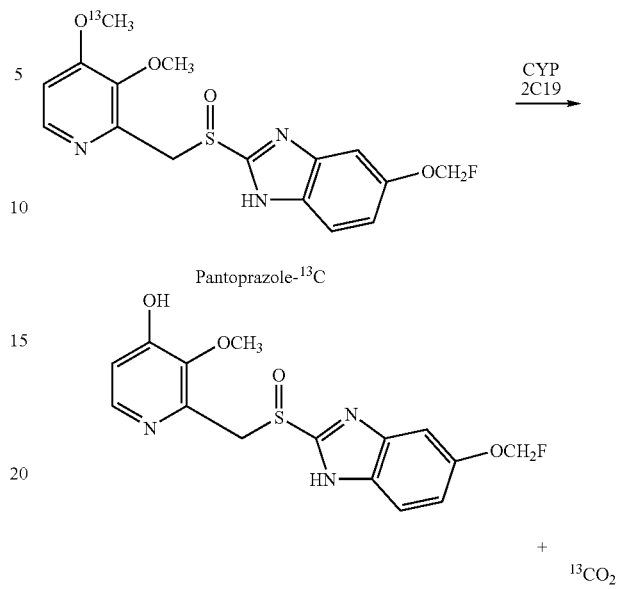

In addition to genetic factors, the apparent phenotype of an individual subject and overall significance of CYP2C19 in the biotransformation of a given substrate is influenced by the quantitative importance of alternative metabolic routes. For example, agents that are preferentially metabolized by CYP2C19, pharmacologic inhibitors can modify enzyme activity such that the magnitude of change in substrate metabolism can mimic that of genetically determined poor metabolizers (i.e., an apparent change in phenotype from an extensive metabolizer to a poor metabolizer). With inhibitors of CYP2C19, the metabolism of coadministered CYP2C19 substrates can be significantly altered in extensive metabolizers. Such interactions can decrease the efficacy of a prodrug requiring metabolic conversion to its active moiety or, alternately, can result in toxicity for CYP2C19 substrates that have a narrow therapeutic index. Non-invasive diagnostic/theranostic tests, e.g., breath tests, are useful to assess the CYP2C19 metabolic status of an individual subject.

The present studies employed the $^{13}CO_2$ breath test method of the present invention to classify individual human subjects (i.e., Volunteers 1-8) by their ability to metabolize Ptz-O-$^{13}CH_3$. Briefly, following an 4-8 h fast normal human subjects ingested 20-200 mg of ptz-O-$^{13}CH_3$ and 2.1 g of sodium bicarbonate to protect the ptz-O-$^{13}CH_3$ from acid degradation in the stomach. A breath sample was collected prior to drug ingestion and then at 5 min time points up to 30 min, at 10 min intervals to 90 min, after ingestion of Ptz-O-$^{13}CH_3$. The breath curves with SD (DOB versus Time (Panel A) and PDR curves with SD versus Time (Panel B)) for eight volunteers for the ptz-O-$^{13}CH_3$ breath test are depicted in FIG. 1

Four volunteers were 2C19 extensive metabolizers (EM), two were 2C19 intermediate metabolizers (IM) and two were poor metabolizers (PM). The present studies demonstrate that either DOB or PDR values at a specific time point are useful to differentiate EM from IM and from PM.

The Ptz-O-$^{13}CH_3$ phenotyping procedure with a $^{13}CO_2$ breath test has several potential advantages over existing phenotyping methods, as mass spectrometry detection can be replaced by infrared spectrometry. In addition to the safety and demonstrated utility of Ptz as a probe for CYP2C19 activity, the breath test affords phenotype determinations within a shorter time frame (1 h or less after Ptz administration) and directly in physicians' offices or other healthcare settings using relatively cheap instrumentation (UBiT-IR$_{300}$ IR spectrophotometer; Meretek).

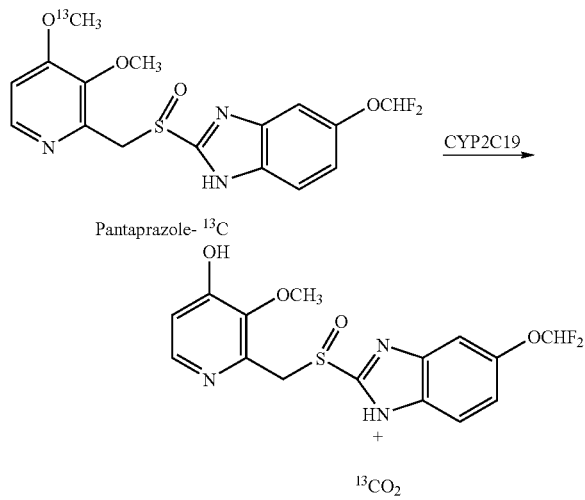

Example 2

Figure 2:
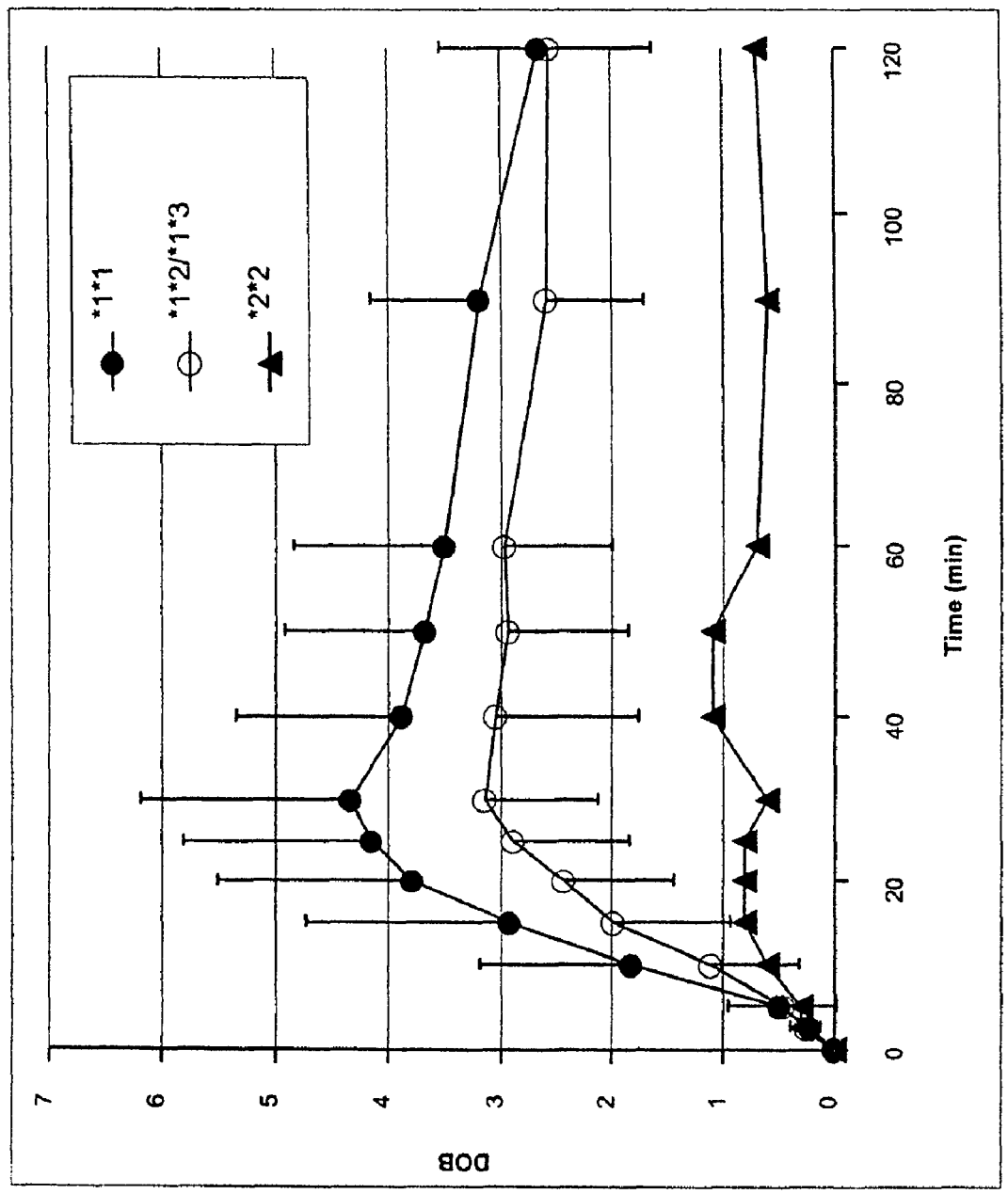
FIG. 2 shows breath curves for ten subjects who were *1*1 (EM), nine subjects who were either *1*2 or *1*3 (IM) and one subject who was *2*2 (PM).

Clinical Study Results Using the $^{13}CO_2$ Breath Test Method of the Invention Twenty subjects were admitted to the GCRC at Indiana School of medicine at about 7 AM following an 8-hour overnight fasting. Baseline breath samples were collected in 1.2-liter aluminum-lined bags (Otsuka Pharmaceuticals, Tokushima, Japan). Subjects were then administered 100 mg pantoprazole-$^{13}C$ (98%; Cambridge Isotope Laboratories Inc., Andover, Mass.) with 2.1 g sodium bicarbonate to prevent gastric acid degradation of the drug and water. Twelve breath samples were collected over 120 minutes (obtained at 2.5, 5, 10, 15, 20, 25, 30, 40, 50, 60, 90, and 120 minutes). All subjects were genotyped. Ten subjects were *1*1 (EM), nine subjects were either *1*2 or *1*3 (IM) and one subject was *2*2 (PM). The breath curves are depicted in FIG. 2.

In one embodiment of the breath test procedure of the invention, $^{13}C$-labeled CYP2C19 substrate compound (0.1 mg-500 mg) is ingested by a subject after overnight fasting (4-12 h), over a time period of approximately 10-15 seconds. Breath samples are collected prior to ingestion of $^{13}C$-labeled CYP2C19 substrate compound and then at 5 min intervals to 30 min, at 10 minute intervals to 90 min, and at 30 min intervals thereafter to 90 min after isotope-labeled substrate ingestion. The breath samples are collected by having the subject momentarily hold their breath for 3 seconds prior to exhaling into a sample collection bag. The breath samples are analyzed on a UBiT IR-300 spectrophotometer (Meretek, Denver, Colo.) to determine the $^{13}CO_2/^{12}CO_2$ ratio in expired breath, or sent to a reference lab.

EQUIVALENTS

The present invention is not to be limited in terms of the particular embodiments described in this application, which are intended as single illustrations of individual aspects of the invention, Many modifications and variations of this invention can be made without departing from its spirit and scope as will be apparent to those skilled in the art. Functionally equivalent methods and apparatuses within the scope of the invention in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled.

We claim:

1. A method for determining cytochrome P450 2C19 isoenzyme phenotype-related metabolic capacity, comprising administering to a mammalian subject a preparation comprising pantoprazole in which at least one of the carbon or oxygen atoms is labeled with an isotope, wherein the preparation produces isotope-labeled $CO_2$ after administration to a mammalian subject, and measuring the excretion pattern of an isotope-labeled metabolite excreted from the body of the subject, thus determining the cytochrome P450 2C19 isoenzyme phenotype-related metabolic capacity.

2. The method according to claim 1, wherein the isotope-labeled metabolite is excreted from the body as isotope-labeled $CO_2$ in the expired air.

3. A method for determining cytochrome P450 2C19 isoenzyme phenotype-related metabolic capacity in a mammalian subject, comprising administering to the mammalian subject a preparation comprising pantoprazole in which at least one of the carbon or oxygen atoms is labeled with an isotope, wherein the preparation produces isotope-labeled $CO_2$ after administration to a mammalian subject, measuring the excretion pattern of an isotope-labeled metabolite excreted from the body of the subject, and assessing the excretion pattern in the subject, thus determining the cytochrome P450 2C19 isoenzyme phenotype-related metabolic capacity in the mammalian subject.

4. The method according to claim 3, further comprising comparing the excretion pattern in the subject or a pharmacokinetic parameter obtained therefrom with the corresponding excretion pattern or parameter in a healthy subject with a normal cytochrome P450 2C19 isoenzyme-related metabolic capacity.

5. A method for determining the presence, absence, or degree of cytochrome P450 2C19 isoenzyme phenotype-related metabolic disorder in a mammalian subject, comprising administering to the mammalian subject a preparation comprising pantoprazole in which at least one of the carbon or oxygen atoms is labeled with an isotope, wherein the preparation produces isotope-labeled $CO_2$ after administration to a mammalian subject, measuring the excretion pattern of an isotope-labeled metabolite excreted from the body of the subject, and assessing the excretion pattern in the subject, thus determining the presence, absence, or degree of cytochrome P450 2C19 isoenzyme phenotype-related metabolic disorder in the mammalian subject.

6. A method for evaluating cytochrome P450 2C19 isoenzyme phenotype-related metabolic capacity, comprising administering a $^{13}C$-labeled pantoprazole to a mammalian subject, measuring $^{13}CO_2$ exhaled by the subject, and determining cytochrome P450 2C19 isoenzyme phenotype-related metabolic capacity from the measured $^{13}CO_2$.

7. The method according to claim 6, wherein the method is non-invasive.

8. The method according to claim 6, wherein the $^{13}C$-labeled pantoprazole is administered intravenously or orally.

9. The method according to claim 6, wherein the exhaled $^{13}CO_2$ is measured spectroscopically.

10. The method according to claim 6, wherein the exhaled $^{13}CO_2$ is measured by infrared spectroscopy.

11. The method according to claim 6, wherein the exhaled $^{13}CO_2$ is measured with a mass analyzer.

12. The method according to claim 6, wherein the exhaled $^{13}CO_2$ is measured over at least three time periods to generate a dose response curve, and the cytochrome 2C19 isoenzyme phenotype-related metabolic activity is determined from the area under the curve or from the delta over baseline value (DOB) at a single timepoint.

13. The method according to claim 6, wherein the exhaled $^{13}CO_2$ is measured over at least two different dosages of the $^{13}C$-labeled pantoprazole.

14. The method according to claim 6, wherein the exhaled $^{13}CO_2$ is measured over at least three time periods to calculate a delta over baseline (DOB), and the cytochrome 2C19 isoenzyme phenotype-related metabolic activity is determined from the DOB.

15. The method according to claim 14, wherein the exhaled $^{13}CO_2$ is measured over at least two different dosages of the $^{13}C$-labeled cytochrome P450 2C19 isoenzyme substrate compound.

16. The method according to claim 6, wherein the exhaled $^{13}CO_2$ is measured over at least three time periods to calculate a percentage dose recovery (PDR), and the cytochrome 2C19 isoenzyme phenotype-related metabolic activity is determined from the PDR.

17. The method according to claim 16, wherein the exhaled $^{13}CO_2$ is measured over at least two different dosages of the $^{13}C$-labeled pantoprazole.

18. The method according to claim 6, wherein the exhaled $^{13}CO_2$ is measured during at least the following time points: $t_0$, a time prior to ingesting the $^{13}C$-labeled pantoprazole; $t_1$, a time after the $^{13}C$-labeled pantoprazole has been absorbed in the bloodstream of the subject; and $t_2$, a time during the first elimination phase.

19. The method according to claim 18, wherein the cytochrome P450 2C19 isoenzyme phenotype-related metabolic capacity is determined from a slope of $\delta^{13}CO_2$ at time points $t_1$ and $t_2$ calculated according to the following equation: slope $=[(\delta^{13}CO_2)_2 - (\delta^{13}CO_2)_1]/(t_2-t_1)$ wherein $\delta^{13}CO_2$ is the amount of exhaled $^{13}CO_2$.

20. The method according to claim 6, wherein a at least one cytochrome P450 2C19 isoenzyme modulating agent is administered to the subject before administrating a $^{13}C$-labeled cytochrome P450 2D6 isoenzyme substrate compound.

21. The method according to claim 20, wherein the cytochrome P450 2C19 modulating agent is a cytochrome P450 2C19 inhibitor.

22. The method according to claim 20, wherein the cytochrome P450 2C19 modulating agent is a cytochrome P450 2C19 inducer.

* * * * *